(12) United States Patent
Koide et al.

(10) Patent No.: US 12,357,560 B2
(45) Date of Patent: Jul. 15, 2025

(54) COMPOSITION FOR TREATING OR PREVENTING SKIN PIGMENTATION

(71) Applicant: Shiseido Company, Ltd., Tokyo (JP)

(72) Inventors: Sayaka Koide, Tokyo (JP); Masaya Takagi, Tokyo (JP); Shoko Yamada, Tokyo (JP); Ritsuro Ideta, Tokyo (JP); Takashi Satoh, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 18/225,377

(22) Filed: Jul. 24, 2023

(65) Prior Publication Data

US 2023/0364006 A1     Nov. 16, 2023

Related U.S. Application Data

(62) Division of application No. 17/298,440, filed as application No. PCT/JP2019/046903 on Nov. 29, 2019, now abandoned.

(30) Foreign Application Priority Data

Nov. 30, 2018   (JP) ................................ 2018-226032

(51) Int. Cl.
    *A61K 8/98*     (2006.01)
    *A61Q 19/02*    (2006.01)

(52) U.S. Cl.
    CPC ............... *A61K 8/985* (2013.01); *A61Q 19/02* (2013.01)

(58) Field of Classification Search
    CPC .......... A61K 35/33; A61K 8/985; A61P 17/00
    See application file for complete search history.

(56) References Cited

U.S. PATENT DOCUMENTS

| | | | |
|---|---|---|---|
| 2008/0025954 A1 | 1/2008 | Lafont et al. | |
| 2009/0047738 A1 | 2/2009 | Shimmura et al. | |
| 2009/0239254 A1 | 9/2009 | Duval et al. | |
| 2010/0124782 A1 | 5/2010 | Ishizuka | |
| 2016/0206551 A1* | 7/2016 | Boss, Jr. ................ | A61K 8/983 |

FOREIGN PATENT DOCUMENTS

| | | |
|---|---|---|
| CN | 106176561 A | 12/2016 |
| JP | 2008-505164 A | 2/2008 |
| JP | 2009-219491 A | 10/2009 |
| RU | 2568059 C1 | 11/2015 |
| WO | WO-2007/061168 A1 | 5/2007 |
| WO | WO-2008/136183 A1 | 11/2008 |

OTHER PUBLICATIONS

Thawabteh et al (Molecules, 2023, vol. 28, pp. 1-28) (Year: 2023).*
Yamaguchi et al (Journal of Cell Biology, 2004, vol. 165, pp. 275-285) (Year: 2004).*
Yoon et al (Theranostics, Sep. 9, 2018, vol. 8, pp. 4620-4632) (Year: 2018).*
Duval et al., "Key Regulatory Role of Dermal Fibroblasts in Pigmentation as Demonstrated Using a Reconstructed Skin Model: Impact of Photo-Aging," PLOS One, Dec. 9, 2014, 9(12):e114182, 25 pages.
Fernandes et al., "Fibroblast sources: Where can we get them?", Cytotechnology, 2016, 68:223-228.
Hedley et al., "Fibroblasts Play a Regulatory Role in the Control of Pigmentation in Reconstructed Human Skin from Skin Types I and II," Pigment Cell Research, Feb. 1, 2002, 15(1):49-56.
Li et al., "Age-associated increase of skin fibroblast-derived prostaglandin E2 contributes to reduced collagen levels in elderly human skin," J. Invest. Dermatol., 2015, 135(9):2181-2188.
Nakade et al., "Involvement of Fibroblast for melanosome excretion in dermis," Fragrance Journal, 2017, 45(1):94-97, with partial English translation, IFSCC2016 Conference on ORLANDO, oral presentation.
Yoshimoto et al., "Mechanism of dermal melanin pigmentation and its application for the development of skin-lightening cosmetics," Cosmetic Stage, Feb. 25, 2017, 11(3):13-15, with partial English translation.
Itaya et al., "The Use of Fibroblasts for Ameliorating Structural Changes Associated with Skin Aging," Rejuvenation Research, Oct. 2017, 20(5):383-388.
Kovacs et al., "Role of fibroblast-derived growth factors in regulating hyperpigmentation of solar lentigo," British Journal of Dermatology, Jul. 19, 2010, 163(5):1020-1027.

* cited by examiner

*Primary Examiner* — Mark V Stevens
(74) *Attorney, Agent, or Firm* — Foley & Lardner LLP (57) ABSTRACT

The present invention provides a composition for treating or preventing skin pigmentation, which contains fibroblasts as an active ingredient, wherein the fibroblasts are those fibroblasts which are less damaged than fibroblasts localized in a site where the skin pigmentation occurs, and the composition is characterized by being intended to be applied to a site where the pigmentation occurs or a dermis tissue around the site.

4 Claims, 9 Drawing Sheets

COMPOSITION FOR TREATING OR PREVENTING SKIN PIGMENTATION

CROSS-REFERENCE TO RELATED APPLICATIONS

This application is a Divisional of U.S. application Ser. No. 17/298,440, which is the U.S. National Stage of PCT/JP2019/046903, filed Nov. 29, 2019, which claims priority to JP 2018-226032, filed Nov. 30, 2018.

FIELD

The present invention relates to a composition for treatment or prevention of skin pigmentation, which includes fibroblasts as an active ingredient.

BACKGROUND

The skin is an organ that covers the surface of the body, separating the interior of the body from its exterior. Skin functions as a physical barrier and protects the interior of the body from dryness and infiltration of hazardous substances, thus performing an indispensable role for life maintenance.

The skin of higher vertebrates primarily consists of the epidermis, dermis and subcutaneous tissue layers, in that order from the outermost layer. The epidermis is composed mainly of cells known as keratinocytes, the keratinocytes dividing at the deepest part (basal lamina) of the epidermis while migrating to the surface and differentiating toward the upper layer into the stratum spinosum, granular layer and stratum corneum, and eventually being shed as old skin.

Melanocytes are present in the basal lamina of the epidermis, with melanin being produced by melanosomes inside the melanocytes. The melanin that is produced is taken up into the surrounding keratinocytes. After being taken up, the melanin migrates to the stratum corneum with turnover of keratinocytes, being discharged out of the body over a period of about 40 days.

It is thought that pigmentation of skin, such as skin spots and freckles, is caused by overproduction of melanin by melanocytes due to hormone imbalance, ultraviolet ray exposure or local inflammation, and by deposition of melanin granules inside keratinocytes in the basal epidermal layer. Methods and agents (skin whiteners) for treatment or prevention of pigmentation such as senile pigmentation spots have been developed, but these have not provided the anticipated effects or have only exhibited temporary effects, resulting in relapse without continual use, and therefore an ongoing demand exists to develop new methods of treatment and prevention, and new therapeutic agents.

Cellular regenerative medicine has come to be developed in recent years, and it is being applied in the field of cosmetics as well. Reference 1, for example, discloses a mixed cell composition comprising melanocytes and fibroblasts to be used for treating skin depigmentation. Reference 2 discloses a method of applying autologous skin fibroblasts for anti-aging and particularly for removal of skin wrinkles.

CITATION LIST

Patent Literature

[PTL 1] International Patent Publication No. 2007/061168
[PTL 2] Chinese Patent Application Publication No. 106176561

SUMMARY

Technical Problem

It is an object of the invention to provide a composition for treatment or prevention of skin pigmentation.

Solution to Problem

As a result of active research by the present inventors, it has been found that skin pigmentation can be treated or prevented if a composition containing fibroblasts with less damage than fibroblasts localized at the site of pigmentation is applied to the surrounding dermal tissue. Specifically, the present invention encompasses the following inventions.

[1] A composition for treatment or prevention of skin pigmentation, containing fibroblasts as an active ingredient, wherein:
the fibroblasts are fibroblasts with less damage than fibroblasts localized at the site of skin pigmentation, and
the composition is applied to the site of pigmentation or its surrounding dermal tissue.

[2] The composition according to [1] above, wherein the pigmentation is from one or more conditions selected from the group consisting of senile pigmentation spots, seborrheic keratosis, Chloasma, freckles and floriform pigmented spots.

[3] The composition according to [1] or [2] above, wherein the fibroblasts are derived from biological tissue of a site with low light exposure or no light exposure.

[4] The composition according to any one of [1] to [3] above, wherein the fibroblasts are derived from a tissue selected from the group consisting of the gluteal region, abdominal region, thorax, femoral region, upper arm, dorsal region, gingiva, oral mucosa, scalp, palms, foot soles and auricle rear.

[5] The composition according to any one of [1] to [4] above, wherein the fibroblasts are autologous fibroblasts.

[6] The composition according to [1] or [2] above, wherein the fibroblasts are fibroblasts differentiated from pluripotent stem cells or tissue stem cells.

[7] The composition according to any one of [1] to [6] above, wherein the fibroblasts have lower expression of a cell senescence marker than fibroblasts localized at the site of pigmentation.

[8] The composition according to [7] above, wherein the cell senescence marker is one or more selected from the group consisting of senescent acidic β-galactosidase (SA-βgal), cell cycle check mechanism-associated factor and cell senescence-associated secretory phenotype (SASP) factor.

[9] The composition according to any one of [1] to [8] above, which is to be applied by cell therapy.

[10] A method for treatment or prevention of skin pigmentation, which includes application of a composition containing fibroblasts as an active ingredient, to a subject in need thereof, wherein:
the fibroblasts are fibroblasts with less damage than fibroblasts localized at the site of skin pigmentation, and
the composition is applied to the site of pigmentation or its surrounding dermal tissue.

[11] A non-therapeutic cosmetic method for reduction or prevention of skin pigmentation, which includes application of a composition containing fibroblasts as an active ingredient, to a subject in need thereof, wherein: the fibroblasts are fibroblasts with less damage than fibroblasts localized at the site of skin pigmentation, and the composition is applied to the site of pigmentation or its surrounding dermal tissue.

Advantageous Effects of Invention

The present invention can treat or prevent excess synthesis of melanin at sites of pigmentation.

BRIEF DESCRIPTION OF DRAWINGS

FIGS. 2A-2B show differences in proliferative ability of fibroblasts treated and not treated with PUVA.

FIGS. 3A-3B show differences in senescence-associated factor SA-β-gal production levels in fibroblasts either treated with PUVA or untreated (control).

FIGS. 4A-4B show differences in production levels of the melanin production promoting factor SCF (Stem Cell Factor) in fibroblasts either treated with PUVA or untreated (control).

FIGS. 6A-6B are diagrams showing pigmentation of a pigmentation skin model either treated or not treated with PUVA.

FIGS. 8A-8B show pigmentation in a pigmentation skin model either treated with PUVA or not treated (control), and a PUVA-treated pigmentation epidermis model, transferred onto a PUVA-untreated dermis model and cultured (Replace).

FIGS. 9A-9B show melanin granules in a pigmentation skin model either treated with PUVA or not treated (control), and a PUVA-treated pigmentation epidermis model, transferred onto a PUVA-untreated dermis model and cultured (Replace).

FIGS. 10A-10B show activated melanocytes in a pigmentation skin model either treated with PUVA or not treated (control), and a PUVA-treated pigmentation epidermis model, transferred onto a PUVA-untreated dermis model and cultured (Replace).

DESCRIPTION OF EMBODIMENTS

Embodiments for carrying out the invention will be described in detail below with reference to the accompanying drawings, with the understanding that the technical scope of the invention is not limited only to these embodiments.

The terms "first, "second" and "third" throughout the present specification are used to distinguish one element from another, and a first element may be referred to as "second element", or similarly a second element may be referred to as "first element", without deviating from the gist of the invention.

Unless otherwise defined, the terms (technical and scientific terms) used herein have the same meanings as generally understood by those skilled in the art.

<Composition for Treatment or Prevention of Skin Pigmentation>

According to one embodiment, the invention provides a composition for treatment or prevention of skin pigmentation containing fibroblasts as an active ingredient, wherein the fibroblasts are fibroblasts with less damage than fibroblasts localized at the site of skin pigmentation, and the composition is applied to the site of pigmentation or its surrounding dermal tissue. The present invention allows excessive synthesis of melanin by melanocytes in the epidermis to be reduced, thus helping to treat or prevent skin pigmentation and being useful in cosmetic methods for reduction and prevention of skin pigmentation as well. Throughout the present specification, the phrase "dermal tissue surrounding the site of pigmentation" means dermal tissue present at the periphery of the site of pigmentation, such as dermal tissue contained in a region within 1 cm, preferably within 5 mm, more preferably within 3 mm and most preferably within 1 mm from the boundary of the site of pigmentation.

It is thought that pigmentation of skin, such as skin spots and freckles, is brought on by overproduction of melanin by melanocytes due to hormone imbalance, ultraviolet ray exposure or local inflammation, and by deposition of melanin granules inside keratinocytes in the basal epidermal layer. Pigmentation is caused by conditions such as senile pigmentation spots, seborrheic keratosis, Chloasma, freckles and floriform pigmented spots. By applying the present invention, therefore, it is possible to reduce excess synthesis of melanin by melanocytes at sites of pigmentation, thus helping to treat or prevent skin pigmentation and being useful in cosmetic methods for reduction and prevention of skin pigmentation as well.

Fibroblasts are one of the types of cells constituting connective tissue, and they are present in a large number of organs and tissues. Fibroblasts produce constituent components of the dermis, including collagen, elastin and hyaluronic acid. The composition of the invention includes fibroblasts having less damage than fibroblasts that are localized at sites of skin pigmentation. The phrase "fibroblasts with less damage than fibroblasts that are localized at the site of skin pigmentation", as used herein, means fibroblasts with less DNA damage than fibroblasts localized at the site of skin pigmentation. DNA, which carries the genetic information in cells, constantly sustains damage by the effects of active oxygen, ultraviolet rays, radiation and/or chemical substances. Such DNA damage is repaired by the function of various DNA reparation mechanisms in the cell. If the frequency of DNA damage exceeds the rate of DNA repair, however, DNA reparation cannot keep up and DNA damage accumulates. This leads to accumulation of DNA mutations in the cell and an increasing state of senescence of the cell.

The phrase "fibroblasts with less damage than fibroblasts that are localized at the site of skin pigmentation" can also be considered to be fibroblasts with lower cell senescence than fibroblasts localized at the site of skin pigmentation. It can also be considered to be fibroblasts with smaller cell sizes and/or higher proliferation than fibroblasts localized at the site of skin pigmentation. Cell senescence can be evaluated by examining the expression of cell senescence markers. Examples of known cell senescence markers include senescent acidic β-galactosidase (SA-βgal), cell cycle check mechanism-related factors (such as $p16^{INK4a}$, $p21^{CIP1}$ and/or p53), and cell senescence-associated secretory phenotype (SASP) factor, and examining the expression of any one or more of these allows different extents of cell senescence to be compared.

SASP factors include, but are not limited to, inflammatory cytokines, chemokines, growth factors and extracellular matrix catabolic enzymes, examples of which include GM-CSF, GRO-α, GRO-β, GRO-γ, IGFBP-7, IL-1α, IL-6, IL-7, IL-8, MCP-1, MCP-2, MIP-1α, MMP-1, MMP-10, MMP-3, amphiregulin, ENA-78, eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, oncostatin M, osteoprotegerin, PIGF, RANTES, sgp130, TIMP-2, TRAIL-R3, Acrp30, angiogenin, Ax1, bFGF, BLC, BTC, CTACK, EGF-R, Fas, FGF-7, G-CSF, GDNF, HCC-4, I-309, IFN-γ, IGFBP-1, IGFBP-3, IL-1 R1, IL-11, IL-15, IL-2R-α, IL-6R, I-TAC, leptin, LIF, MMP-2, MSP-a, PAI-1, PAI-2, PDGF-BB, SCF, SDF-1, sTNF RI, sTNF RII, thrombopoietin, TIMP-1, tPA, uPA, uPAR, VEGF, MCP-3, IGF-1, TGF-β, MIP-1-delta, IL-4, FGF-7, PDGF-BB, IL-16, BMP-4, MDC, MCP-4, IL-10, TIMP-1, Flt-3 ligand, ICAM-1, Ax1, CNTF, INF-γ, EGF and BMP-6. Different degrees of cell senescence can be compared by examining expression levels of one or more of these factors.

The method for quantifying a cell senescence marker may be any publicly known method including, but not being limited to, ELISA, real-time PCR, Western blotting, Northern blotting, flow cytometry methods and microarray methods, which are methods allowing different expression levels of cell senescence markers to be compared. A composition containing fibroblasts with less damage than fibroblasts localized at the site of skin pigmentation, such as fibroblasts with a lower expression level of a cell senescence marker than fibroblasts localized at the site of pigmentation, can be applied to the site of pigmentation or its surrounding dermal tissue to treat or prevent pigmentation.

According to one embodiment, fibroblasts used for the invention may be fibroblasts derived from biological tissue with low light exposure or no light exposure. The phrase "biological tissue with low light exposure or no light exposure", as used herein, means a site that is covered by clothes or hair during most of the time period of daily living activities of a human and has relatively low frequency of exposure to light (compared to the face, for example), and examples of such tissues include tissue from the gluteal region, abdominal region, thorax, femoral region, dorsal region, gingiva, oral mucosa, scalp, palm, foot soles and auricle rear regions. Fibroblasts derived from tissue with low light exposure are preferred because they have a low frequency of exposure to light, and especially ultraviolet rays, and therefore have a low degree of damage.

According to one embodiment, the fibroblasts to be used for the invention may be primary fibroblasts obtained by fine cutting of biological tissue and treatment with proteases such as collagenase or trypsin, or fibroblasts grown by subculturing of the obtained primary human fibroblasts. According to one embodiment, the fibroblasts used for the invention may be ones cultured using a publicly known medium.

According to another embodiment, the fibroblasts used for the invention may be autologous fibroblasts. Autologous fibroblasts are preferred because they are not rejected by immunoreaction when applied to a subject.

According to another embodiment, fibroblasts used for the invention may be fibroblasts differentiated from pluripotent stem cells or tissue stem cells. The pluripotent stem cells used may be iPS cells, ES cell or Muse cells, and it is possible to use fibroblasts obtained by inducing differentiation by a publicly known method, or fibroblast progenitor cells (including mesenchymal stem cells, for example) obtained by a differentiation-inducing process.

Throughout the present specification, "dermal tissue (or dermis)" is tissue present between the epidermis and subcutaneous tissue of skin, being composed mainly of fibroblasts, collagen, elastic fibers (elastin), extracellular matrix and hyaluronic acid. The composition of the invention may be applied to a site of pigmentation or its surrounding dermal tissue to directly or indirectly act on melanocytes within the site of pigmentation and reduce overproduction of melanin. The method of applying the composition of the invention may be carried out by any means known in the technical field for providing cell therapy, such as injection of the suspended composition with a syringe.

The composition of the invention may also include a pharmaceutically acceptable carrier in addition to the fibroblasts. As used herein, "pharmaceutically acceptable carrier" means a diluent, adjuvant, excipient or vehicle that is approved by a domestic regulatory agency and can be used for animals, and particularly humans. According to one embodiment, carriers that may be added to the composition of the invention include, but are not limited to, physiological buffer solutions, injectable gel solutions, physiological saline and water. Examples of physiological buffer solutions that may be used for the invention include, but are not limited to, buffered saline, phosphate buffered solutions, Hank's balanced salt solution, Tris-buffered saline and HEPES buffered saline.

An injectable gel solution to be used for the invention may be in the form of a gel before injection, or it may be one that gels after injection. An injectable gel solution is composed of water, physiological saline or physiological buffered solution, and a gelling substance, for example. Examples of gelling substances include, but are not limited to, proteins (such as collagen, elastin, thrombin, fibronectin, gelatin, fibrin, tropoelastin, polypeptides, laminin, proteoglycans, fibrin pastes, self-assembling peptide hydrogels and atelocollagen), polysaccharides (such as pectin, cellulose, oxidized cellulose, chitin, chitosan, agarose and hyaluronic acid), polynucleotides (such as ribonucleic acid and deoxyribonucleic acid), alginates, crosslinked alginates, poly(N-isopropyl acrylamide), poly(oxyalkylene), poly(ethylene oxide)-poly(propylene oxide) copolymer, poly(vinyl alcohol), polyacrylate, monostearoylglycerol cosuccinate/polyethylene glycol (MGSA/PEG) copolymer, and combinations of the foregoing.

The number of fibroblasts included in the composition of the invention is not restricted since it may be appropriately set depending on the size of the pigmentation to which it is to be applied, the degree of pigmentation, the age of the subject, the condition being treated and the method of application.

<Method of Evaluating of Composition for Treatment or Prevention of Skin Pigmentation>

The composition of the invention can be evaluated using the pigmentation skin model $1a$ shown in FIGS. 1A-1F, for example. The evaluation can be carried out by a method that includes the following procedure, for example.

(1) A step of damaging fibroblasts 100 with photoirradiation and then culturing them (FIG. 1A),
(2) a step of culturing the fibroblasts 100 obtained in step (1) on a first cell culture insert 11 (FIG. 1B),
(3) a step of culturing a cell group 200 including melanocytes 202 and keratinocytes 201 on a second cell culture insert 21 (FIG. 1C),
(4) a step of setting the second cell culture insert 21 in which the fibroblasts 100 obtained in step (2) have been cultured, onto the fibroblasts 100 obtained in step (2), and culturing them (FIG. 1D),
(5) a step of culturing a composition 300 on a third cell culture insert 31 (FIG. 1E),
(6) a step of transferring the second cell culture insert 21 in which the fibroblasts 100 obtained in step (4) have been cultured, onto the third cell culture insert 31 in which the composition 300 obtained in step (5) has been cultured, and culturing them (FIG. 1F), and
(7) a step of evaluating the treatment or prevention effect of the composition 300, using the extent of pigment production and/or pigmentation in the cell group 200 including the melanocytes 202 and keratinocytes 201 obtained in step (6) as an indicator.

Throughout the present specification, the first cell culture insert 11 in which the fibroblasts 100 have been cultured and the third cell culture insert 31 in which the composition 300 has been cultured may be referred to as "dermis models" (first dermis model 10 and second dermis model 30), since they model the structure of the skin dermis. Also throughout the present specification, the structure containing the cell group 200 may be referred to as "epidermis model 20" since it models the structure of the skin epidermis.

The fibroblasts 100 are preferably photoirradiated in the presence of a photosensitizer to induce damage. Examples of photosensitizers to be used include psoralen, NAD, riboflavin, tryptophan, folic acid, porphyrin, methylene blue, and thiol group-protected gold nanoclusters (AUxSRy). By using a photosensitizer it is possible to cause sensitization to the irradiated light and more efficiently induce damage in the fibroblasts 100.

The light used to induce damage in the fibroblasts 100 may have a wavelength which causes damage in intracellular nucleic acid such as DNA or RNA but does not result in death of all of the cells, and it is preferably ultraviolet light (about 200 nm to about 400 nm), and more preferably UVA (about 320 nm to about 400 nm). The intensity of the irradiated light may be such as to produce damage in the intracellular nucleic acid such as DNA or RNA while not inducing apoptosis and death in all of the cells, and it can be appropriately adjusted by the wavelength or irradiation time, and the cell density. Irradiation of UVA, for example, may be at 0.01 J/cm$^2$ to 100 J/cm$^2$, preferably 0.1 J/cm$^2$ to 20 J/cm$^2$ and more preferably 0.5 J/cm$^2$ to 10 J/cm$^2$.

Figure 1A:
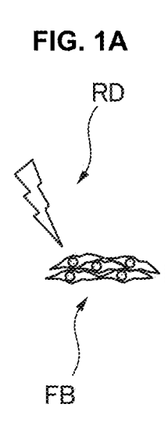
FIGS. 1A-1F are a schematic diagram showing a method of evaluating a composition of the invention. The constituent elements are shown mainly in cross-sectional form.
Figure 1B:
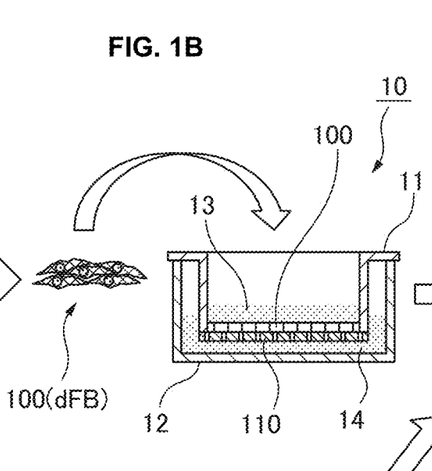

If the photoirradiated fibroblasts are cultured for a fixed time period it is possible to cause proliferation of only the surviving fibroblasts 100 that have not undergone apoptosis (FIG. 1A). Fibroblasts that have suffered damage by photoirradiation have elongated cellular forms and reduced proliferation potency, as well as increased production of senescence-associated factors (senescence-associated acidic β-galactosidase (SA-β-gal)) and melanin-producing factors (such as stem cell growth factor (SCF) and hepatocyte growth factor (HGF)), and thus an increased level of cell senescence (see FIGS. 2A-2B, FIGS. 3A-3B, FIGS. 4A-4B and FIG. 5). The level of cell senescence can be evaluated by measuring these cell senescence markers. Adjustment of the photoirradiation dose allows fibroblasts 100 with the desired level of cell senescence to be obtained.

The second cell culture insert 21 has a smaller inner diameter than the first cell culture insert 11 and third cell culture insert 31. This will allow the second cell culture insert 21 to be used by insertion into the culture portions of the first cell culture insert 11 and third cell culture insert 31.

The cells used in the pigmentation skin model 1 may be derived from any animal, but they are preferably derived from a vertebrate, more preferably from a mammal, and most preferably from a human.

The fibroblasts 100 used in the pigmentation skin models (1, $1a$) are preferably fibroblasts derived from the dermis.

The keratinocytes 201 are a type of cells composing the epidermis, and in biological epidermal tissue they divide at the deepest part (basal lamina) while migrating to the surface and differentiating toward the upper layer into the stratum spinosum, granular layer and stratum corneum, eventually being shed as old skin.

The melanocytes 202 are a type of cells composing epidermal tissue, which are present in the epidermal basal lamina of biological tissue and produce melanin.

The fibroblasts 100, keratinocytes 201 and melanocytes 202 used in the pigmentation skin models (1, $1a$) may each be primary cultured cells harvested from biological tissue, or cells marketed or distributed after first having been isolated and/or grown, or cells of an established cell line, or cells differentiated from pluripotent stem cells such as ES cells, iPS cells or Muse cells.

The first dermis model 10 may also contain cells other than fibroblasts 100, such as mast cells, histiocytes, plasmocytes or dermal dendritic cells that are present within dermal tissue. The number of fibroblasts in the first dermis model 10 may be $1 \times 10^4$ to $10^8$/cm$^2$, and preferably 0.1 to $10 \times 10^5$/cm$^2$.

The first dermis model 10 preferably has the fibroblasts 100 seeded together with a hydrogelling agent. As used herein, "hydrogelling agent" is a substance added in order to form a hydrogel. Hydrogelling agents to be used for the invention may be selected from the group consisting of collagen, gelatin, hyaluronate, hyaluronan, fibrin, alginate, agarose, chitosan, chitin, cellulose, pectin, starch, laminin, fibrinogen/thrombin, fibrillin, elastin, gum, cellulose, agar, gluten, casein, albumin, vitronectin, tenascin, entactin/nidogen, glycoproteins, glycosaminoglycan, poly(acrylic acid)

and its derivatives, poly(ethylene oxide) and its copolymers, poly(vinyl alcohol), polyphosphazene, Matrigel, and combinations of the foregoing.

Step (2) may be carried out in the presence of ascorbic acid or a salt thereof. Ascorbic acid or a salt thereof is preferably present in order to promote multilayer formation similar to the structure of the dermis, by accelerated proliferation of the fibroblasts 100 and collagen production. Throughout the present specification, "ascorbic acid" refers to ascorbic acid or its derivative (such as ascorbic acid diphosphate, ascorbic acid monophosphate, sodium L-ascorbate and L-ascorbic acid 2-glucoside), as well as its salts (such as sodium salts and magnesium salts).

The cell group 200 may also include cells other than the keratinocytes 201 and melanocytes 202, such as Langerhans cells in the epidermal tissue, or Merkel cells. The cell group 200 may include the cells in a proportion of keratinocytes 201:melanocytes 202 of 1:1 to 1000:1 and preferably 30:1 to 3:1. The cell group 200 includes the keratinocytes 201 at $1 \times 10^2$ to $10^6/cm^2$, preferably 1.0 to $10 \times 10^4/cm^2$ and more preferably about 4 to $8 \times 10^4/cm^2$, and the melanocytes 202 at 1 to $10 \times 10^3/cm^2$ and preferably 4 to $8 \times 10^3/cm^2$.

The epidermis model 20 may employ TESTSKIN® LSE-melano (TOYOBO) and MelanoDerm® (MatTek), for example, which are commercially available.

The pigmentation skin model 1 may be cultured using a culture solution commonly used as a culture solution for culturing of keratinocytes, such as KG medium, EpilifeKG2 (Kurabo Industries, Ltd.), Humedia-KG2 (Kurabo Industries, Ltd.) or assay medium (TOYOBO), at about 37° C. for a period of 0 to 30 days. The culture medium used may alternatively be DMEM culture medium (Gibco), or a culture medium comprising a 1:1 mixture of ascorbic acid-containing KGM and DMEM.

The pigmentation skin model 1 has fibroblasts damaged by photoirradiation that has acted directly or indirectly on melanocytes, accelerating melanin production. The pigment production and/or extent of pigmentation in the pigmentation skin model 1 can then be measured to evaluate factors that affect pigmentation.

As used herein, "pigment production" refers to production of a pigment such as melanin pigment, which is produced by the pigmentation skin model. Melanin pigment is produced primarily by melanocytes. The amount of pigment production can be determined as the amount of melanin, by extracting the melanin pigment from the pigmentation skin model, and especially the second cell group (keratinocytes and melanocytes), and measuring the absorbance at 405 nm. The amount of pigment production can be measured as the level of melanin or nucleic acid (such as mRNA) coding therefor, present in the pigmentation skin model and particularly the second cell group (keratinocytes and melanocytes), using a method such as ELISA, flow cytometry, Western blotting, an immunohistochemical method or qPCR, with no limitation to these.

As used herein, "extent of pigmentation" means the color brightness of the pigmentation skin model, and particularly the second cell group (keratinocytes and melanocytes), under visible light. The pigmentation skin model of the invention has varying brightness depending on the amount of melanin produced by the melanocytes. A greater amount of melanin results in reduced brightness, so that the pigmentation skin model exhibits a darker color. A lower amount of melanin, conversely, increases the brightness and causes the pigmentation skin model to exhibit a lighter color. That is, the treatment or prevention effect on pigmentation by an added candidate substance can be evaluated by comparing the color brightness of the pigmentation skin model. The brightness can be quantified by recording the pigmentation skin model as an image and using publicly known image measuring means.

EXAMPLES

The present invention will now be explained in greater detail by examples, with the understanding that the invention is not limited in any way by the examples.

1. Materials and Methods Used 1-1. Fibroblast Culturing and PUVA Treatment

Normal human fibroblasts ($1 \times 10^5$ cells) were cultured with a growth medium (DMEM+10% fetal calf serum). Before reaching 100% confluence, the medium was exchanged with growth medium containing psoralen (final concentration: 25 ng/mL) (Sigma-Aldrich), and culturing was continued. After 24 hours, the cells were imbibed with 1 mL phosphate-buffered saline (PBS), the PBS was removed, the medium was exchanged with 1 mL PBS containing psoralen (final concentration: 25 ng/mL), and UVA irradiation (SAN-EI UVE-5025) was carried out at 6 $J/cm^2$ (hereunder this will be referred to as "PUVA treatment"). This was followed by imbibing with 1 mL PBS and then removal of the PBS, exchange with growth medium, and continued culturing for about 2 to 7 days. Some of the cells died by the effects of PUVA treatment during the procedure, with the surviving fibroblasts continuing to proliferate. Fibroblasts from the same donor without PUVA treatment were used as a control in comparison with the PUVA-treated fibroblasts (FIGS. 2 to 5).

1-2. Preparation of Dermis Model

A dermis model was prepared using fibroblasts subjected to the PUVA treatment of 1-1. above, or without PUVA treatment (control). Briefly, the procedure of 1. above was followed by removal of the growth medium and imbibing with 1 mL PBS. The PBS was then removed, a cell release agent (TrypLE SELECT, Thermo Fisher Scientific) was added at 300 µL per well of a 6-well plate, and the mixture was allowed to stand for 5 minutes in a 5% $CO_2$ incubator at 37° C. as cell releasing treatment. Growth medium was added to suspend the reaction, and the cell suspension was recovered in a 15 ml centrifuge tube. After centrifugation at 1000 rpm for 5 minutes, the supernatant was removed and the cell pellet was resuspended in growth medium and adjusted to $5 \times 10^5$ cells/mL. A gel suspension comprising the composition listed in Table 1 was prepared on ice to prepare a dermis model for application to each well of a 6-well plate.

TABLE 1

Composition of gel suspension for dermis model containing fibroblasts

| Reagent | Amount |
| --- | --- |
| Pig skin collagen (final concentration: 0.5% (w/v)) (NH Foods Ltd., 309-31595) | 1.5 mL |
| 5 × DMEM | 0.6 mL |
| Fetal bovine serum (final concentration: 10% (v/v)) | 0.3 mL |
| L-ascorbic acid 2-glucoside(AA2G) (final concentration: 250 µM) (Sigma-Aldrich, SMB00390) | 3 µL |
| Fibroblast suspension | 0.6 mL |
| Total volume | 3 mL |

A cell culture insert for dermis model preparation was set in the 6-well plate and 3 mL of gel suspension was added into the cell culture insert. After solidifying the gel suspension with a 5% $CO_2$ incubator at 37° C., 2 mL of growth medium containing ascorbic acid (AA2G) was added to the 6-well plate and culturing was carried out for 24 hours in the 5% $CO_2$ incubator at 37° C.

1-3. Pigmentation Skin Model Combined with Epidermis Model

Figure 1C:
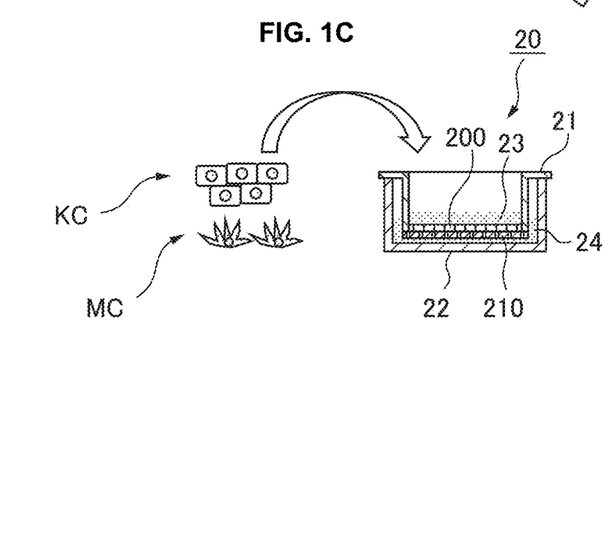
Figure 1D:
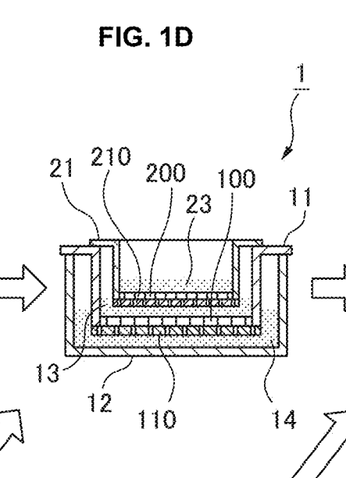

Separately from the dermis model, a commercially available epidermis model (MatTek Co.) comprising melanocytes and keratinocytes was also used (see FIG. 1C).

The epidermis model was laid over and combined with the dermis model of 1-2. above (see FIG. 1D) and set in a specialized vessel (Corning BioCoat deep well plate, 6 wells) (Corning #355467), and then 9.5 mL of three-dimensional skin model medium (a 1:1 mixture of epidermis model special medium (MatTek #EPI-100-NMM-113) and DMEM) was added and medium exchange was carried out with the same medium at a frequency of once every 3 to 4 days.

1-4. Pigmentation Skin Model with Replaced Dermis Model

Figure 1E:
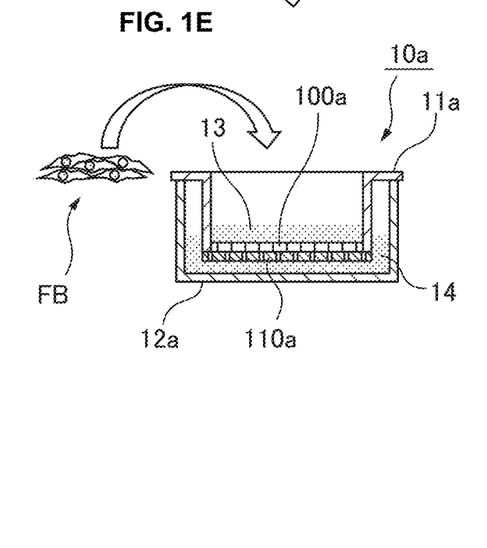
Figure 1F:
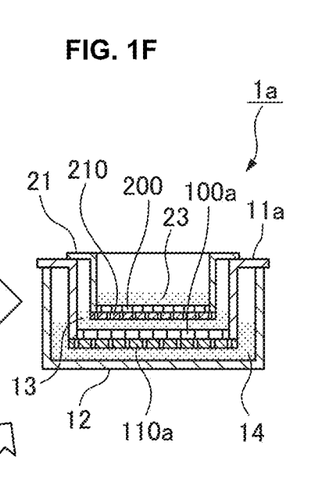

An epidermis model cultured for 10 days in combination with a dermis model prepared using PUVA-treated fibroblasts was replaced with a dermis model prepared using PUVA-untreated normal fibroblasts, and culturing was continued for 10 days (see FIGS. 1E and 1F). The replacement dermis model (dermis model prepared using PUVA-untreated fibroblasts) was prepared on the day prior to replacement.

2. Results 2-1. PUVA-Treated Fibroblasts

Figure 2A:
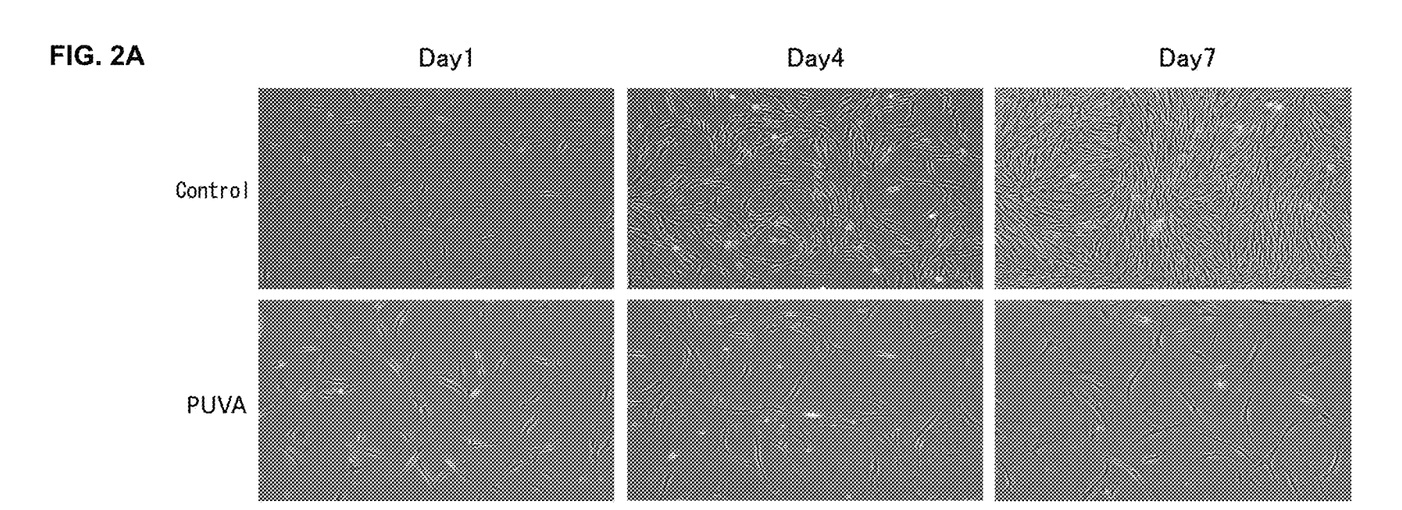
FIG. 2A: Image of monolayer cultured fibroblasts either treated with PUVA or not treated (control) (day 1, 4 and 7 of culturing).
Figure 2B:
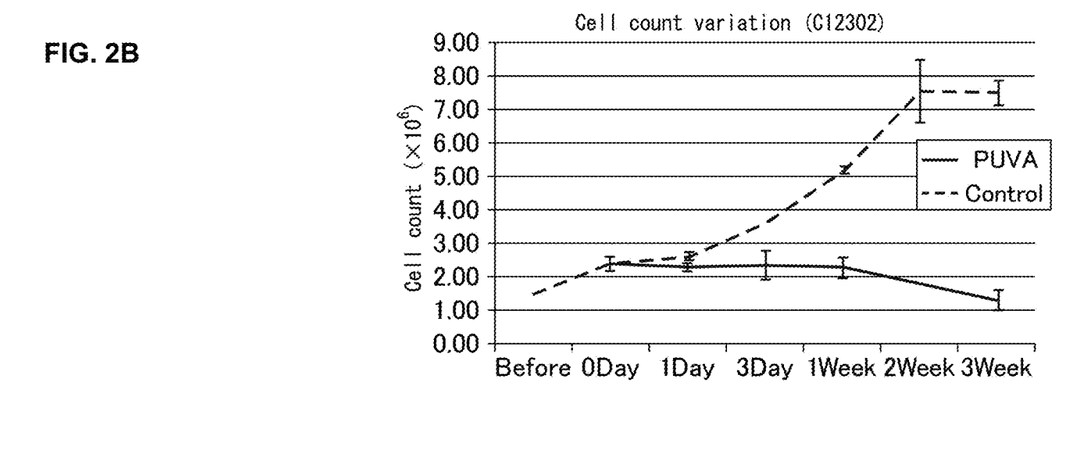
FIG. 2B: Proliferation graph of fibroblasts after PUVA treatment.

FIGS. 2A-2B shows PUVA-treated and untreated fibroblasts. The PUVA-treated fibroblasts had become elongated (FIG. 2A). Upon examining variation in the number of proliferated PUVA-treated and untreated fibroblasts, it was found that the PUVA-treated fibroblasts had a notably lower growth rate (FIG. 2B).

2-2. Senescence Level of PUVA-Treated Fibroblasts

Figure 3A:
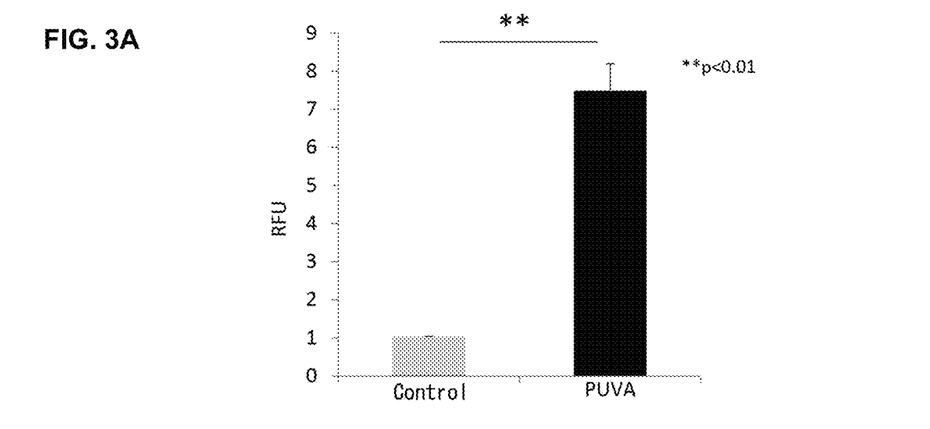
FIG. 3A: Enzyme activity values of SA-β-gal in monolayer cultured fibroblast lysates.
Figure 3B:
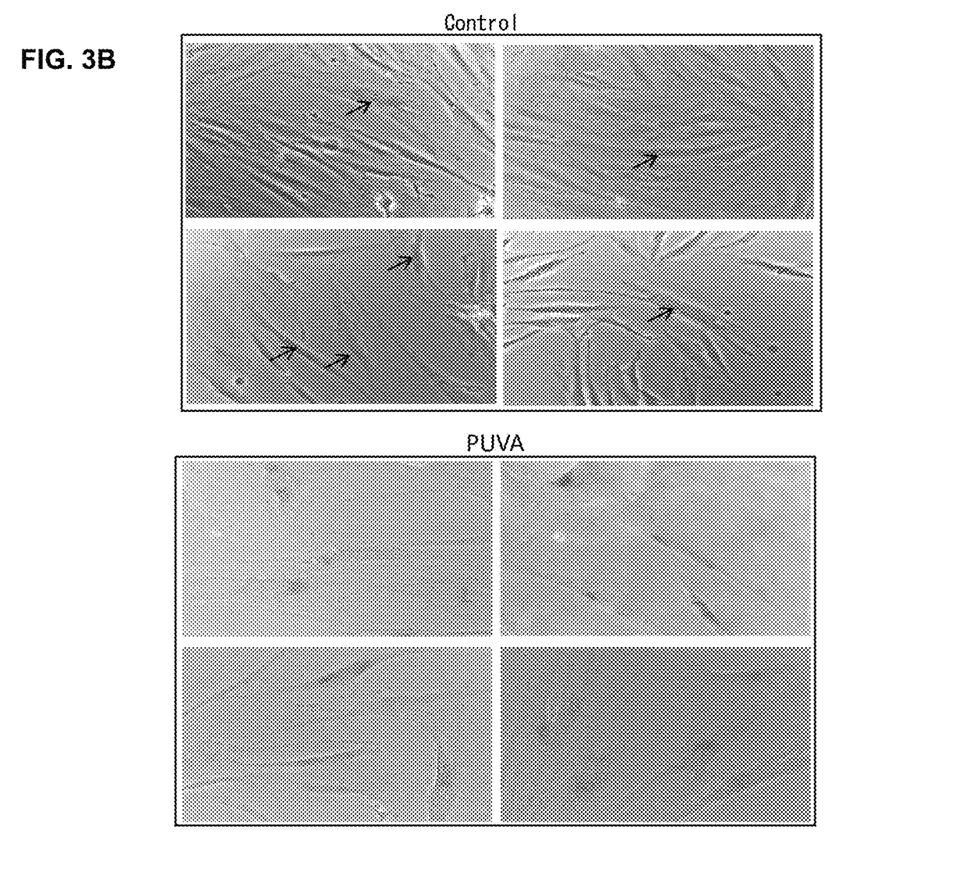
FIG. 3B: SA-β-gal stained images. The SA-β-gal positive cells are stained turquoise.

Upon examining the enzyme activity values of senescence-associated factor SA-β-gal in cell lysates of PUVA-treated and untreated fibroblasts, it was found that the PUVA-treated fibroblasts had notably increased SA-β-gal enzyme activity (FIG. 3A). With SA-β-gal staining, the PUVA-treated fibroblasts were observed to have a very large number of SA-β-gal positive cells (turquoise) (FIG. 3B).

Figure 4A:
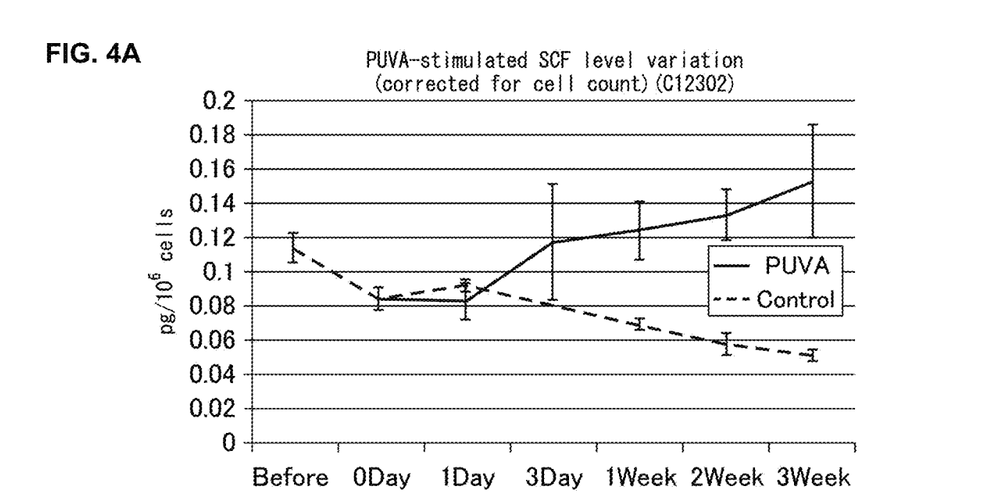
FIG. 4A: Graph showing variation in SCF production with time.
Figure 4B:
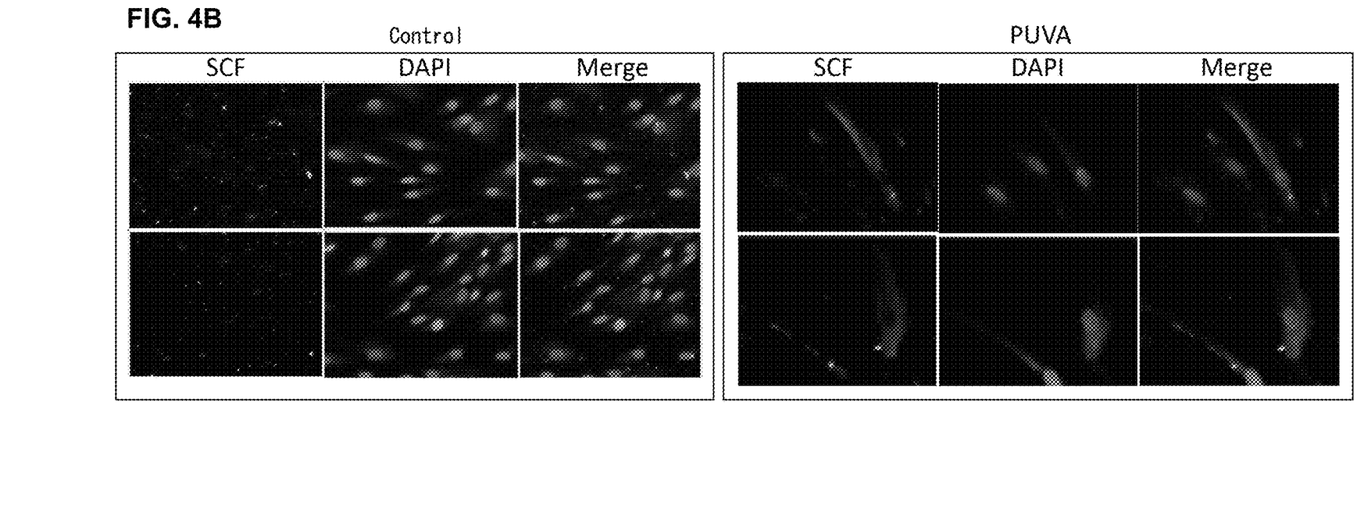
FIG. 4B: SCF staining with SCF antibody, nuclear staining with DAPI, and fused (merged) image of SCF staining and nuclear staining (2 each).

2-3. Production Level of Melanin-Producing Factor SCF in PUVA-Treated Fibroblasts When the PUVA-treated and untreated fibroblasts were each cultured by monolayer culture, with measurement of the SCF amounts in the culture supernatants 1 day before PUVA treatment and 0, 1, 3, 7, 14 and 21 days after PUVA treatment by ELISA, and calculation of the amount of secretion per cell, the SCF level of the PUVA-treated fibroblasts was found to be notably higher (FIG. 4A). When SCF staining with SCF antibody and nuclear staining with DAPI were carried out and a fused (merged) image for the SCF staining and nuclear stain was created, a large number of SCF-positive cells were observed among the PUVA-treated fibroblasts (FIG. 4B).

Figure 5:
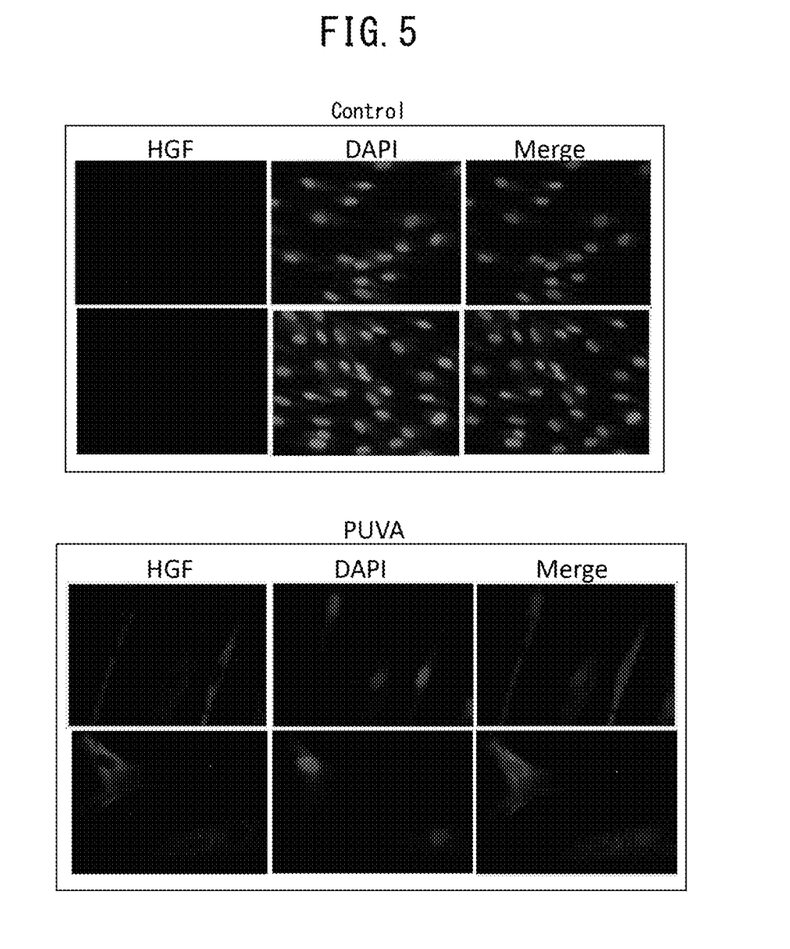
FIG. 5 shows differences in production levels of the melanin production promoting factor HGF (Hepatocyte Growth Factor) in fibroblasts either treated with PUVA or untreated (control). (A) HGF staining with HGF antibody, nuclear staining with DAPI, and fused (merged) image of HGF staining and nuclear staining (2 each).

2-4. Production Level of Melanin-Producing Factor HGF in PUVA-Treated Fibroblasts When PUVA-treated and untreated fibroblasts were each cultured by monolayer culture, and then HGF staining with HGF antibody and nuclear staining with DAPI were carried out and a fused (merged) image for the HGF staining and nuclear stain was created, a large number of HGF-positive cells were observed among the PUVA-treated fibroblasts (FIG. 5(A)).

Figure 6A:
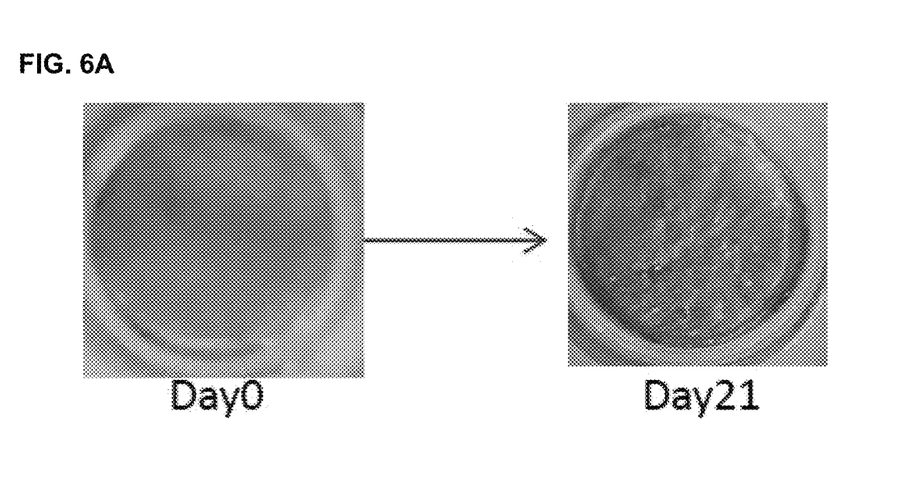
FIG. 6A: Epidermis model image, for a pigmentation skin model treated with PUVA (day 0 and day 21 of culturing).
Figure 6B:
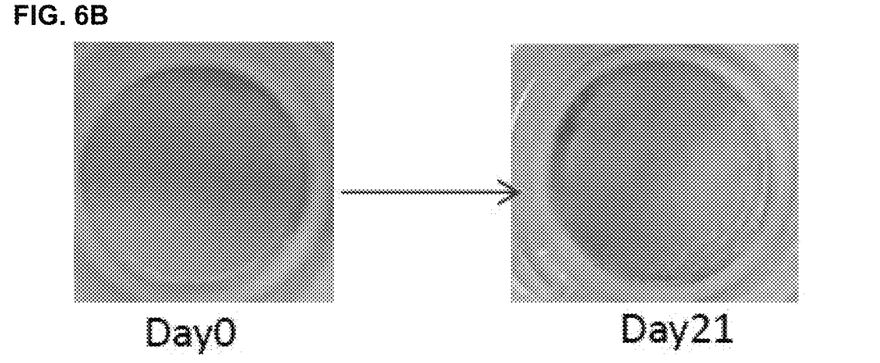
FIG. 6B: Epidermis model image, for a pigmentation skin model not treated with PUVA (day 0 and day 21 of culturing).

2-5. Production Level of Melanin-Producing Factor HGF in PUVA-Treated Fibroblasts FIGS. 6A-6B are diagrams showing pigmentation in an epidermis model, for a pigmentation skin model either with PUVA treatment (FIG. 6A) or without treatment (FIG. 6B). The epidermis model for the PUVA-treated pigmentation skin model showed accelerated pigmentation.

2-6. Pigmentation Skin Model with Replaced Dermis Model

Figure 7:
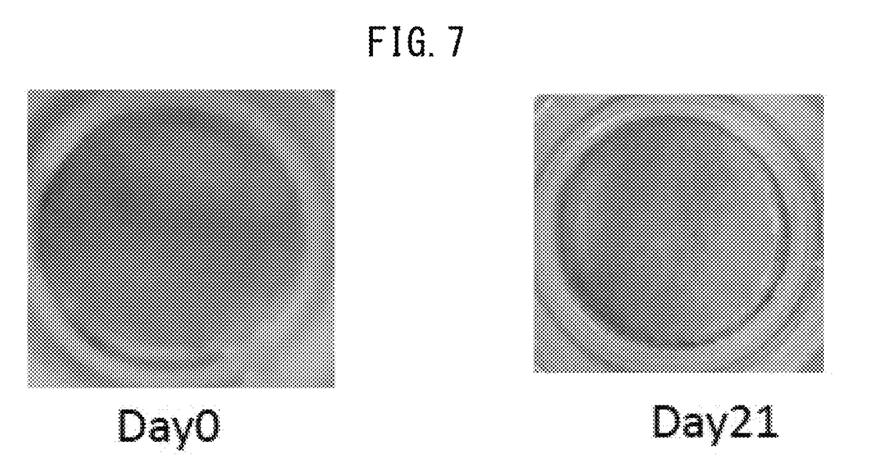
FIG. 7 is an image of an epidermis model, prepared by co-culturing an epidermis model for approximately 10 days with a PUVA-treated dermis model, and then transferring onto a PUVA-untreated dermis model and culturing for approximately 10 days.

An epidermis model cultured for 10 days in combination with a dermis model prepared using PUVA-treated fibroblasts was replaced with a dermis model prepared using PUVA-untreated normal fibroblasts, and after culturing for another 10 days, pigmentation was observed to be inhibited (FIG. 7) compared to pigmentation in the epidermis model for the PUVA-treated pigmentation skin model (FIG. 6A).

Figure 8A:
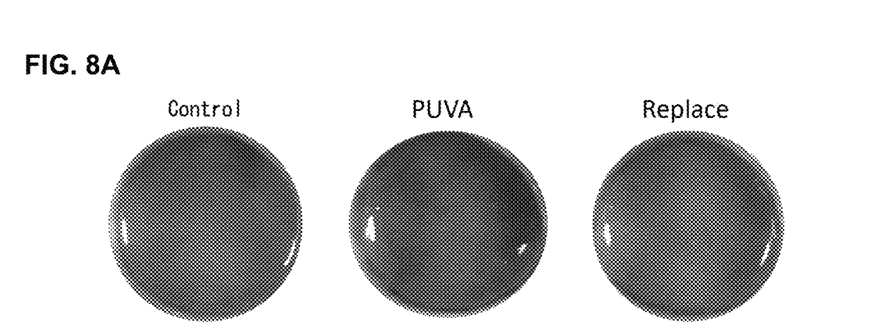
FIG. 8A: Image of epidermis model photographed after fixing the observation conditions in the bright field of a phase contrast microscope.
Figure 8B:
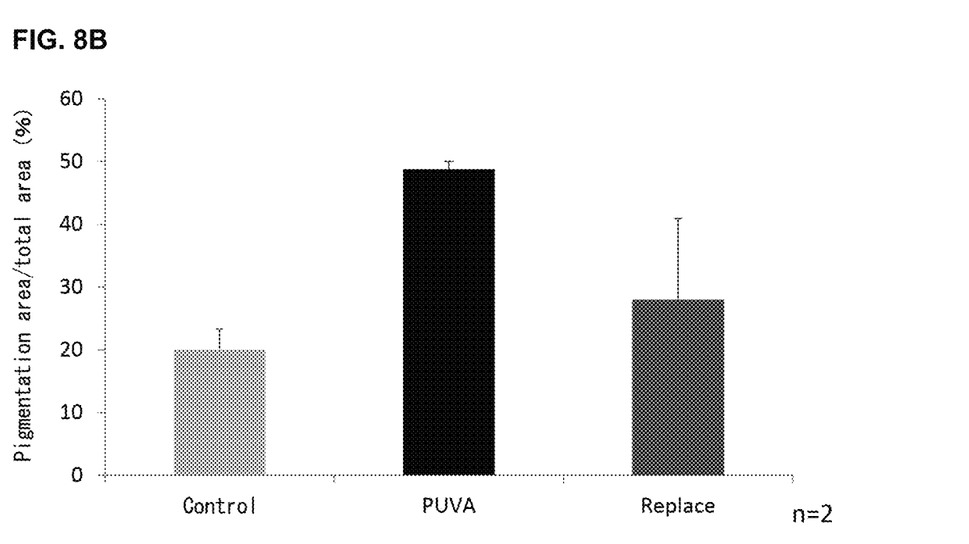
FIG. 8B: Graph showing binarization of image (FIG. 8A), with quantification of the pigmentation area percentage.

2-7. Pigmentation in Pigmentation Skin Models with PUVA Treatment, without Treatment, and with Dermis Model Replacement A PUVA-treated or untreated (control) pigmentation skin model, and an epidermis model which was an epidermis model of a PUVA-treated pigmentation skin model transferred onto a PUVA-untreated dermis model and cultured (Replace), were outwardly observed, and as a result the pigmentation in the epidermis model of the PUVA-treated pigmentation skin model was found to be accelerated while pigmentation in the epidermis model under the Replace conditions was alleviated (FIG. 8A). Upon quantification based on the image of FIG. 8A, the ratio of the thickest pigmented region in the PUVA-treated pigmentation skin model was high, while the region of thick pigmentation in the pigmentation skin model under the Replace conditions was reduced (FIG. 8B).

Figure 9A:
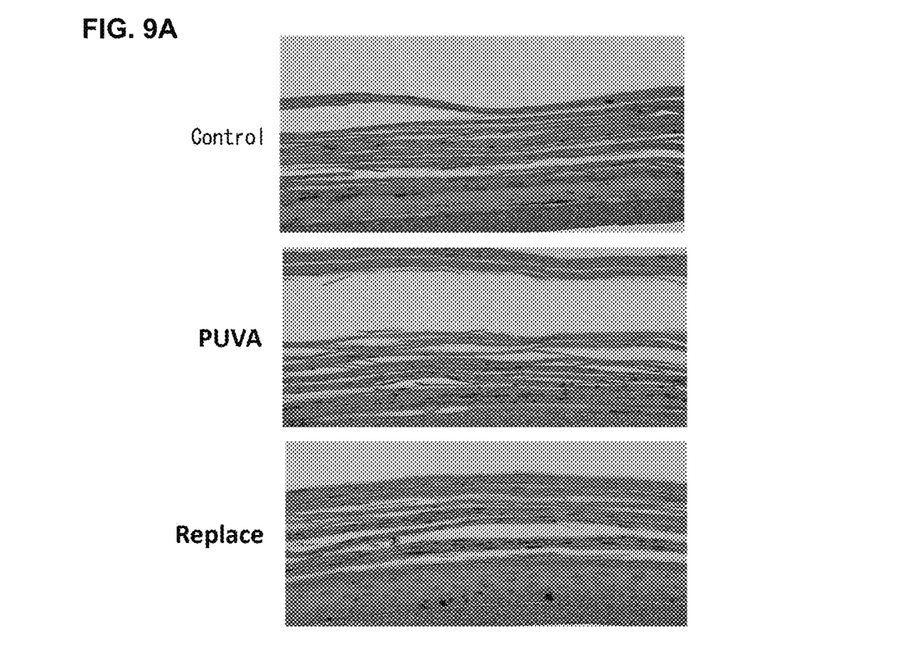
FIG. 9A: Staining of melanin granules in epidermis model slice by Fontana-Masson staining.
Figure 9B:
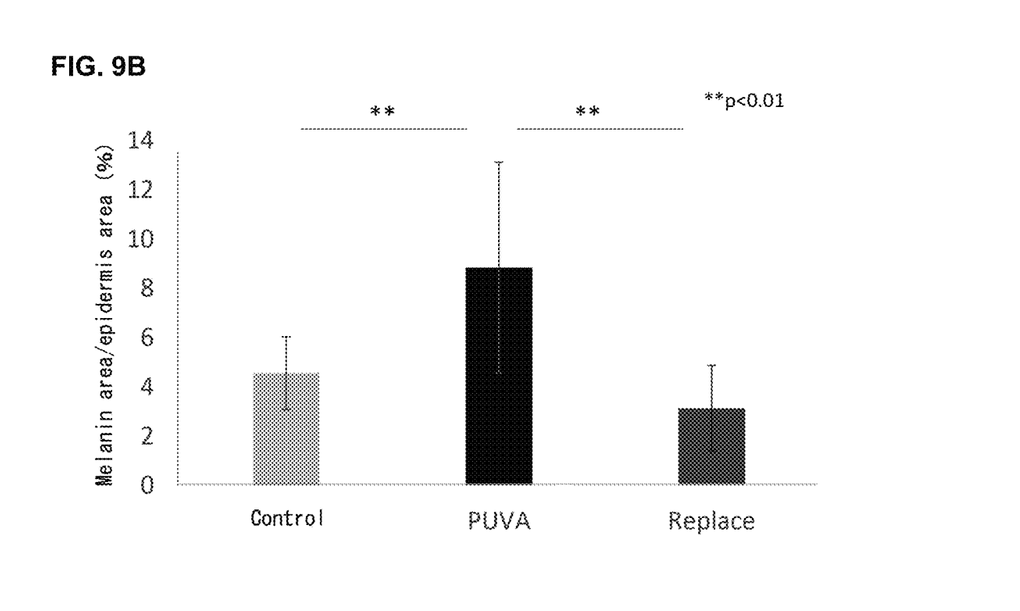
FIG. 9B: Graph showing binarization of image (A), with quantification of the melanin granule area percentage.

2-8. Melanin Formation in Pigmentation Skin Model with PUVA Treatment, without Treatment, and with Dermis Model Replacement After preparing slices of a PUVA-treated or untreated (control) pigmentation skin model, and an epidermis model which was a PUVA-treated pigmentation skin model replaced on a PUVA-untreated dermis model and cultured (Replace), the melanin granules in the epidermis model slices were stained by Fontana-Masson staining (FIG. 9A). When the stained image of FIG. 9A was binarized and the ratio of melanin granule regions was quantified, it was found that the ratio of melanin regions was highest in the PUVA-treated pigmentation skin model, while the melanin regions in the pigmentation skin model under the Replace conditions were reduced (FIG. 9B).

Figure 10A:
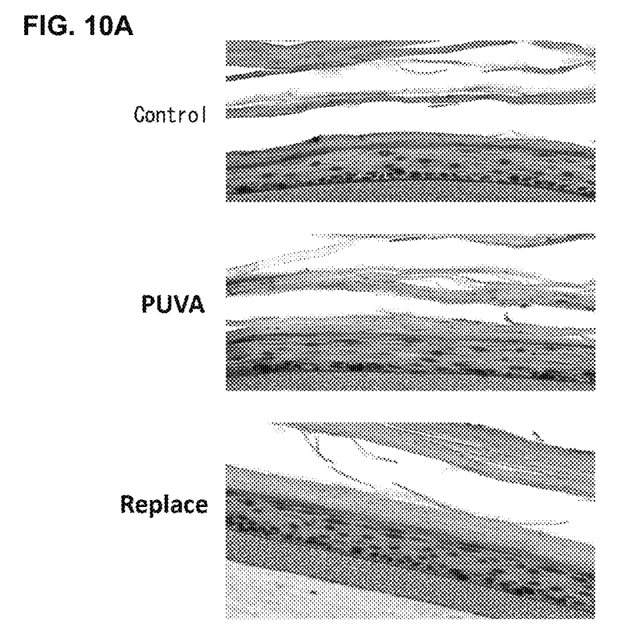
FIG. 10A: Image of activated melanocytes in epidermis model slice stained using TRP2 (Tyrosine Related Protein 2) antibody, and nuclear-stained by hematoxylin staining.
Figure 10B:
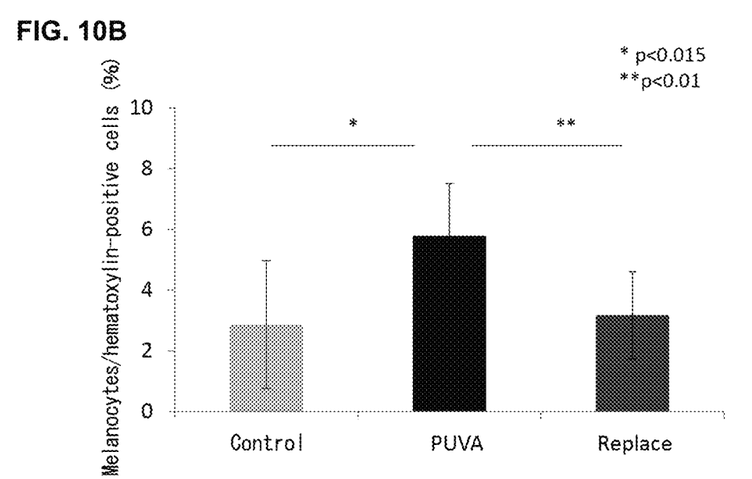
FIG. 10B: Graph showing quantified percentage of activated melanocytes from image (FIG. 10A).

2-9. Number of Melanocytes in Pigmentation Skin Model with PUVA Treatment, without Treatment, and with Dermis Model Replacement After preparing slices of a PUVA-treated or untreated (control) pigmentation skin model, and an epidermis model which was a PUVA-treated pigmentation skin model replaced on a PUVA-untreated dermis model and cultured (Replace), TRP2 antibody was used for staining of the activated melanocytes in the epidermis model slices, and the nuclei were stained by hematoxylin staining (FIG. 10A). When the ratio of activated melanocytes was quantified from the image of FIG. 10A, it was found that the ratio of activated melanocytes was highest in the PUVA-treated pigmentation skin model, while the number of activated melanocytes in the pigmentation skin model under the Replace conditions was reduced (FIG. 10B).

REFERENCE SIGNS LIST 1, 1a Pigmentation skin model
10 First dermis model

100 Fibroblasts
11 First cell culture insert
12 First cell culturing vessel
13 First medium
14 Second medium
20 Epidermis model
200 Cell group containing melanocytes and keratinocytes
201 Keratinocytes
202 Melanocytes
21 Second cell culture insert
22 Second cell culturing vessel
23 Third medium
24 Fourth medium
30 Second dermis model
300 Composition
31 Third cell culture insert
32 Third cell culturing vessel
RD Photoirradiation
dFB Fibroblasts damaged by photoirradiation

The invention claimed is:

1. A method for treatment of skin pigmentation of a subject in need thereof, the method comprising:
applying fibroblasts as an active ingredient to a site of skin pigmentation or a surrounding dermal tissue of the subject, wherein:
the fibroblasts are fibroblasts with less damage than fibroblasts localized at the site of skin pigmentation,
the fibroblasts have lower expression of a cell senescence marker than fibroblasts localized at the site of skin pigmentation,
the fibroblasts are derived from a tissue selected from the group consisting of a gluteal region, an abdominal region, a thorax, a femoral region, an upper arm, a dorsal region, a gingiva, an oral mucosa, a scalp, and an auricle rear,
the cell senescence marker is one or more selected from the group consisting of senescent acidic β-galactosidase (SA-βgal), cell cycle check mechanism-associated factor and cell senescence-associated secretory phenotype (SASP) factor, and
the skin pigmentation is caused by activated melanocytes induced by photo damaged-fibroblasts.

2. The method according to claim 1, wherein the pigmentation is from one or more conditions selected from the group consisting of senile pigmentation spots, seborrheic keratosis, Chloasma, freckles and floriform pigmented spots.

3. The method according to claim 1, wherein the fibroblasts are autologous fibroblasts.

4. The method of claim 1, wherein the skin pigmentation is caused by overproduction of melanin by melanocytes due to ultraviolet ray exposure.

* * * * *